United States Patent [19]

Wall et al.

[11] 4,225,542
[45] Sep. 30, 1980

[54] EVAPORATIVE HUMIDIFIER

[75] Inventors: Thomas H. Wall, St. Paul; Kevin T. Johnson, Minneapolis, both of Minn.

[73] Assignee: Minnesota Mining and Manufacturing Company, St. Paul, Minn.

[21] Appl. No.: 968,829

[22] Filed: Dec. 12, 1978

Related U.S. Application Data

[63] Continuation of Ser. No. 817,799, Jul. 21, 1977, abandoned.

[51] Int. Cl.² .................... B01F 3/04; A61M 15/00
[52] U.S. Cl. ................................. 261/142; 219/275; 261/70; 261/104; 261/131; 261/154; 261/DIG. 65
[58] Field of Search ................. 261/70, 104, 107, 131, 261/142, 153, 154, DIG. 65; 128/186, 188, 192-194; 219/271-276, 306, 307, 311, 362

[56] References Cited

U.S. PATENT DOCUMENTS

| | | | |
|---|---|---|---|
| 2,653,017 | 9/1953 | Frost | 261/104 X |
| 3,092,442 | 6/1963 | Shoemaker | 261/104 X |
| 3,167,601 | 1/1965 | Schlising | 261/154 |
| 3,355,155 | 11/1967 | Heltzen et al. | 261/154 X |
| 3,438,372 | 4/1969 | Sugg et al. | 261/DIG. 65 |
| 3,836,129 | 9/1974 | Perelmutr et al. | 261/DIG. 65 |
| 3,954,920 | 5/1976 | Heath | 261/DIG. 65 |
| 4,051,205 | 9/1977 | Grant | 261/DIG. 65 |
| 4,110,419 | 8/1978 | Miller | 261/142 |

Primary Examiner—Richard L. Chiesa
Attorney, Agent, or Firm—Cruzan Alexander; Donald M. Sell; Edward T. Okubo

[57] ABSTRACT

A sterilizable evaporative humidifier for respiratory usage having a disposable absorbent evaporative element is disclosed. The humidifier provides humidification, low pressure drop and a very short warm-up period. Electronic controls are provided to ensure safe automatic operation.

5 Claims, 2 Drawing Figures

EVAPORATIVE HUMIDIFIER

This is a continuation of application Ser. No. 817,799 filed July 21, 1977, and now abandoned.

BACKGROUND OF THE INVENTION

It is well known in the art that humidifiers are used with respiratory equipment to both warm and humidify the breathing gas provided to a patient. The breathing gas can be oxygen, air, anesthetic gas or mixtures thereof.

Frequently, the breathing gas is composed of a mixture of air and augmenting oxygen. It has been found to be much simpler to have the breathing apparatus control the volume of only one of the gases and have the correct ratio of the other gas provided by aspiration through a venturi aspirator. In order for this mixing technique to operate correctly, the back pressure in the system must be minimized. Many humidifiers provide excessive back pressure so that their use in conjunction with a venturi-type oxygen mixing aspirator is impractical.

Another area of concern in humidifier design is to provide equipment which can be sterilized and/or incorporate elements which are replaced after usage to prevent transfer of contagion between patients. Conditions within a respiratory circuit are conducive to very rapid growth of pathogenic microorganisms which can be carried into the circuit during the patient's exhalation cycle and thrive and multiply within the warm, moist atmosphere. If the assembly is not thoroughly sterilized before reuse, contagion can be easily blown directly into the next patient who may be in weakened condition and thus ill equipped to cope with same.

Still another area of concern in the design of respiratory humidifiers is to provide a unit which will provide adequate heating and humidification for a wide range of gas flows from the very low flow required for infants to the highest flow required by adults. The humidifier unit should also be capable of supplying almost instant heating and humidification so that it is ready for instant use in an emergency without the need for a warm-up period and so that steady state can be reached quickly minimizing temperature variations resulting from an extended warm-up period which can vary from 10 minutes to as along as 60 minutes in presently available humidifiers.

Respiratory systems frequently incorporate an artificial breathing apparatus which generates pulses of breathing gas to the patient through flexible connective tubing. The breathing apparatus can provide either pulses of a given pressure or of a given volume. The apparatus can be set to provide pulses which are adjusted to fit the particular patient, whether juvenile with small lung capacity or adult with large lung capacity. Normally the breathing apparatus is located some distance away from the patient so that the interconnecting tubing comprises a considerable volume which makes accurate control of the pulses difficult. The humidifier is normally located intermediate along the interconnecting delivery tubing so that the internal volume of the humidifier also contributes more or less significantly to the interconnection volume. Accordingly, it would be advantageous to make the internal volume of the humidifier as small as possible.

When the humidifier is used in conjunction with an artificial breathing apparatus it will obviously have pulses of breathing gas passing through it. These pulses of gas have an instantaneous flow rate which starts at zero at the beginning of the pulse, increases to a maximum value, and decreases again to zero at the end of the pulse. This maximum flow rate is termed the "peak inspiratory flow rate."

A humidifier can typically accommodate peak inspiratory flow rates that exceed its maximum continuous flow rate since the humidifier pre-heats the volume of gas residing within the humidification chamber between pulses in addition to heating the pulsed gas as it passes through the humidifier. The "dead" or resident gas will thus be heated to a higher temperature than the "pulses" gas and will be mixed in the humidification chamber, the mixed humidified gases at the humidifier outlet being generally of uniform temperature and pulsatile.

Medical humidifiers generally fall into three types or classifications: (1) Nebulizers or droplet spray types, (2) Bubbler types, and (3) Evaporative or steam types. Other types or variations have been proposed from time to time but the three categories which will be discussed are those which are most widely used and accepted at the present time.

(1) NEBULIZERS

Nebulizers are devices which are used for two different but sometimes combined purposes. In its simplest form, liquid is drawn from a reservoir through a tube terminating in a nozzle at whose exit port the stream is broken into fine droplets by a passing gas flow in much the same manner as the well-known atomizers used to spray many common household liquid products. Nebulizers are useful for delivering a fine fog of liquid medicament to a patient along with the respiratory gas stream. The droplet particle size somewhat determines whether the fog will be deposited within the upper or lower respiratory tract. When used for humidification rather than for inhalation therapy, some nebulizer designs incorporate baffles to separate larger droplets, incorporate heating, or use other means in an attempt to remove or evaporate the droplets of water. None of the methods used to date has been entirely satisfactory in completely removing water droplets from the gas stream. Not only can excessive droplets have a traumatic effect upon a weakened patient, but the droplets also provide a vehicle for transport of microorganisms into the patient's respiratory system. Such microorganisms are not readily transported by humid gas in the absence of water droplets. It is also difficult to provide warming of respiratory air to a physiologically acceptable temperature in an atomization process.

(2) BUBBLER HUMIDIFIERS

These humidifiers usually function by blowing the air through a tube and allowing it to exit near the bottom of a water reservoir and then bubble up through the water. Since the normal ascension of bubbles through a short water distance would not provide sufficient humidification and/or heating of the gas bubbles, these units are usually equipped with baffles, porous packing or the like to break up the bubbles into smaller sizes and to slow their travel. The water can be heated in a bubbler humidifier. Probably the greatest drawback of bubbler humidifiers is the pressure required to force the air down to the bottom of the liquid reservoir, such pressure drop effectively precluding the use of oxygen/gas venturi mixers.

(3) EVAPORATIVE HUMIDIFIERS

This type of humidifier is the most recent in design and is rapidly gaining in acceptance because of its advantages over the two previously mentioned types of humidifiers.

In their simplest form, evaporative humidifiers allow the gas to pick up humidity through passage of the gas over a wetted surface. Efficiency, as measured by humidity increase, can be increased by increasing the area of wetted contact either in terms of two-dimensional area or by increasing surface porosity or texture. It can be further enhanced by heating the water, directly or indirectly, or by heating the evaporative surface, or by heating the air. Further increase in evaporation can be obtained through increasing the air velocity or by other means of increasing turbulence at the interface. Heating of the air by the evaporative surface can be accomplished by super-saturation of the air thereby warming the air but which, however, also can result in fog formation. Evaporative humidifiers provide advantages over the other types of humidifiers by providing higher humidity per unit volume without producing water droplets.

SUMMARY OF THE INVENTION

The present invention comprises an evaporative humidifier with a humidification chamber of about 200 cc. internal volume having an inlet connection port and an exit connection port for gases, a liquid reservoir and a removable porous evaporative element of open-ended cylindrical design which fits loosely within the humidification chamber when dry but which swells into good thermal contact with the side walls of the chamber when wet and which extends into the liquid reservoir. The chamber is tightly surrounded by a heating element so that heat is transferred directly to the chamber walls adjacent to the porous removable evaporative element and not to the liquid reservoir. The heating element is preferentially equipped with suitable electronic controls to monitor the heat transfer surface temperature, and to shut the unit off when said temperature exceeds a predetermined level. The humidifier is designed so that the gases reaching the patient will be at 100% relative humidity under most conditions of gas flow and heater temperature settings.

BRIEF DESCRIPTION OF THE DRAWINGS

In the accompanying diagrammatic drawings which illustrate the invention.

DETAILED DESCRIPTION OF THE INVENTION

Figure 1:
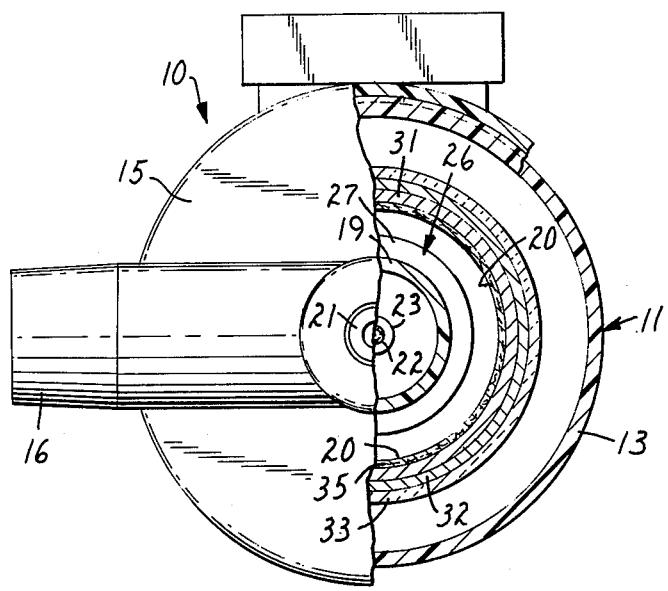
FIG. 1 is a top plan view, partly in section, of the humidifier of the present invention.
Figure 2:
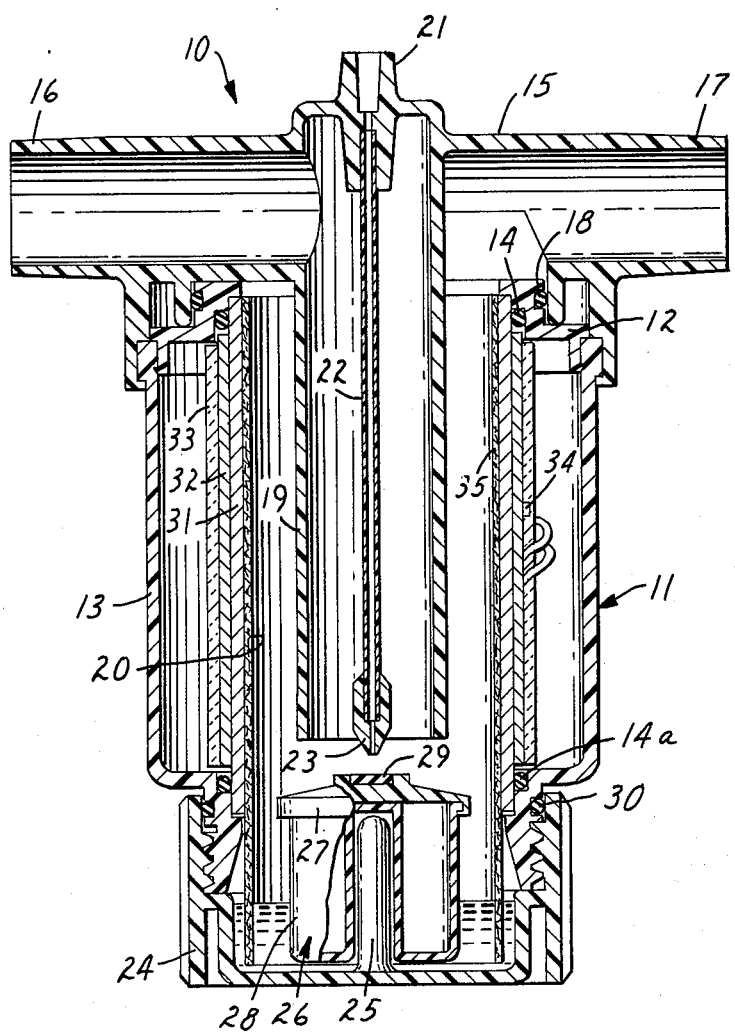
FIG. 2 is a sectional view of the humidifier of the present invention.

Referring now more particularly to the drawings, humidifier 10 comprises a generally cylindrical housing 11, including a central humidification chamber 20 having an internal volume of about 200 cc. a removable air flow cap assembly 15 to which appropriate tubing (not shown) would be assembled, and a removable bottom cap assembly 24. Air flow cap assembly 15 is frictionally and mechanically assembled to the top of housing 11 by a bayonet fastener with an O-ring 18 providing a leak-proof seal. Air inflow connector 16 and air outflow connector 17, which are sized so that the customarily used corrugated respiration tubing can be quickly and easily connected thereon, are integrally formed as part of cap assembly 15 as shown in FIG. 1. Depending from cap assembly 15 is an air flow directing tube 19, which serves to direct the inflowing air from air inflow connector 16 into the interior of humidifier 10 such that the inflowing air must flow upwardly along most of the length of the humidification chamber 20 and the evaporative element 35. Water inlet connector 21 is also integrally formed as a part of cap assembly 15 and a water supply tube 22 depends from water inlet connector 21. Air flow cap assembly 15 may be provided with an exit gas temperature sensing element (not shown) such as a thermistor which would monitor the temperature of the exiting gas and shut off the heating element when the temperature exceeds a pre-set level. Air flow cap assembly 15 which is removable from the housing 11 of the humidifier 10 facilitates cleaning and/or sterilization of the assembly. Alternatively, air flow cap assembly 15 could be formed as an integral part of the humidifier housing 11, with only the bottom cap 24 being removable. Cap assembly 15 is preferably molded of 20% glass filled polypropylene, although it cold be fabricated from die-cast metal or other polymeric materials such as Nylon, Epoxy, etc. However, it is preferred that the material utilized be capable of withstanding repeated steam sterilization cycles. Less durable materials should be gas sterilizable.

The air flow directing tube 19 has a cross-sectional area comparable in size to that of the air inflow connector 16 so that excessive pressure drop is not experienced. Pressure drop in the humidifier of the present invention is very small being on the order of about 0.1 cm. of water at a continuous flow rate of 30 liters per minute. For similar reasons, the space between said air flow directing tube 19 and the surrounding evaporative element 35 should be of comparable cross-sectional area. The air flow directing tube 19 is shown extending close to the bottom of the humidification chamber 20 so that the air must travel upwardly along most of the length of the evaporative element 35. Efficiency would be reduced only slightly if the tube were shortened and compensatory means could be accomplished through shaping the tube exit into a slightly restricted nozzle or into a shape which would provide a circular or cyclonic gas discharge with only a slight additional pressure drop. Alternatively, the gas flow could be reversed, i.e., flowing in from the right of FIG. 1, downwardly around the air flow directing tube 19, up through the air flow directing tube 19, and exit to the left. Still other air flow paths are considered within the scope of the present invention such as air inflow or air outflow at the top or bottom of the humidifier 10.

Water inlet connector 21, shown at the top of humidifier 10 in FIG. 1, is adapted for connection to a supply tube (not shown) from a source of distilled water such as an I.V. container supported at a higher location for gravity flow. Water supply tube 22 is constructed of 0.125 inch O.D., 0.069 inch I.D. type "316" stainless steel tubing. For better flow restriction, a valve tip 23 is provided at the bottom of the water supply tube 22 with a restricted opening of 0.020 inch I.D. It is also to be considered within the scope of the invention to provide an enlarged bottom water reservoir which can allow the unit to function for a prolonged single usage period without the need for an external water supply connection, provided that such water reservoir is so located that the water in the reservoir will not be in contact with heater tube 31.

In the preferred embodiment shown, bottom cap 24 functions as the liquid reservoir. A central upstanding guide stem 25 integrally formed in bottom cap 24 serves to position the float 26, while allowing the float to freely move upward or downward with the level of the liquid in the reservoir. The float 26 has a valve seat 29 which shuts off the flow of water from the valve tip 23 when the water level in the reservoir reaches a predetermined level.

The bottom cap 24 is preferably molded of clear, unfilled polycarbonate so that the presence or absence of water in the reservoir can be visually observed. The cap is threaded into engagement against a sealing O-ring 30 so that it can be easily removed or replaced without the need for tools and so that it will provide leak-proof engagement. Of course, the bottom cap 24 can be molded as an integral part of the housing 11 in which event the air flow cap 15 would be removable for cleaning of the humidifier 10 and replacement of the evaporative element 35. This would be the preferred construction in the enlarged water reservoir single use embodiment.

The float assembly 26 is normally made up of two separate clear polycarbonate elements, a top 27 and a body 28, bonded together in leak-proof fashion by, for example, ultrasonic welding. Of course, an adhesive may be used to bond the two elements together. The float top 27 includes a valve seat 29 of 0.06 inch thick silicone rubber typically retained in place by a suitable adhesive.

Housing 11 is also formed of 20% glass filled polypropylene and carries a removable heater tube 31 constructed of 1.875 inch O.D. aluminum tubing. Wrapped around the exterior of the heater tube 31 and preferably vulcanized thereto is a water-proof 200 watt, 120 volt electric heater element 32 in the form of a blanket embedded in silicone rubber. Covering the heater blanket 32 is a thermal insulating layer 33 which is preferably a 1/16 inch thick silicone sponge rubber layer. Also attached to the heater blanket 32 is at least one temperature sensing element such as a thermistor 34.

Housing 11 is constructed in two parts which are fitted together as by a plurality of latching fingers spaced around and depending from the periphery of annular top section 12. O-ring 14 provides a seal between said annular top section 12 and body member 13. Heater blanket 32 and heater tube 31 are permanently mounted and "sealed" in housing 11. An O-ring 14a provides a substantially leak-proof seal around the bottom periphery of tube 31. Alternatively, the entire outer cavity could be filled with thermal insulation, e.g. foamed in placed insulation.

Humidifier 10 of the present invention is intended to be connected to a separate unit containing appropriate electronic controls and electrical power supply connections. It is, of course, contemplated that the electronic controls could be sealed within the housing 11, in waterproof fashion so that the only external connection accessory necessary would be the electrical supply cord. The electronic controls, of conventional design, perform the necessary functions to turn the humidifier "on" and "off," monitor and control the temperature of the heat transfer surface of heater tube 31, and the temperature of the gases reaching the patient. The heat transfer surface temperature of heater tube 31 is sensed by the thermistor 34 embedded in the heating blanket 32. This information is fed into a thermostatic control circuit in the electronic controls which maintains the temperature constant at the selected setting. The range of heat transfer surface temperatures which may be selected is from about 40° to 100° C.

In the event that the heat transfer surface temperature exceeds a certain pre-determined temperature (say 127° C. or 139° C.) a "thermal cut-out" device (not shown) provided in the heater blanket 32 will melt and open the heater circuit to shut off the heating element 32. The primary (and possibly the only) situation where this would occur would be failure of the thermostatic control circuit in such a way that the heating element would be turned fully on. The thermal cut-out device will thus protect the humidifier housing 11 from melting or burning.

It has been empirically determined that the evaporative element or wick 35 should be disposable so that it can be removed, discarded and replaced after each usage thereby removing a potential source of contamination. Since cost of a disposable item is an important commercial consideration, wick 35 should be fabricated from relatively inexpensive materials.

With the present evaporative concept whereby the evaporative element or wick 35 is in a direct short-path contact with the heat transfer surface of heater tube 31, the evaporation rate is much enhanced and the evaporation rate per unit area is quite high allowing use of a very small evaporative surface. With this high rate of evaporation per unit area, it is necessary that the wicking rate be likewise high so that the rapidly evaporated water is quickly replaced. Unfortunately materials having good wet-strength characteristics usually have reduced wicking rates because the water-resistant reinforcing materials impart reduced hydrophilicity to the reinforced structure.

Unexpectedly, it has been found that when certain types of paper are used, they tend to swell greatly when wetted thereby increasing their outside diameter. Paper is, of course, a desirable material due to its low cost and because its natural hydrophilicity contributes to good wicking action. In order to take full advantage of this phenomenon, it is imperative that both the wick 35 and heat transfer surface of heater tube 31 be either cylindrical or frustroconical and that the wick fit inside of the heat transfer surface so that wick 35 can be undersized when dry and swell into good intimate thermal contact when wet.

The preferred form of wick 35 comprises a laminate of two layers of absorbent materials, the inner layer having good stiffness and dimensional integrity, especially when wet, and the outermost layer having good wicking and swelling properties. In this embodiment, wick 35 comprises an outer layer of Scott Hi-Loft 3055 non-woven paper, 55 pounds basis weight, purchased from Scott Paper Company, Chester, Pa., and an inner layer of James River—Pepperell, Inc., P 2212, Grade 06101A, Bleached Absorbent Wet Strength Kraft paper having a basis weight of about 95 pounds. Lamination can be accomplished by adhesive bonding, heat sealing, needle-looming, etc., but must not result in a complete moisture barrier between the two layers of the laminate since the outer highly absorbent layer must be able to transfer water horizontally to the inner layer so that the relatively slower wicking inner layer need not depend wholly on its own vertical wicking ability to remain wet as water is evaporated from it. The horizontal transfer of water is one of the primary purposes of the highly absorbent outer layer. To prevent formation of a complete moisture barrier between layers, any adhesive or heat sealing material is applied in the form of thin strips or dots.

After the materials are bonded together, the resultant laminate is formed on a cylindrical mandrel or folded, with the edges slightly overlapped or butted together and sealed by taping, heat sealing, sewing, or other appropriate means. Wicks 35 are then cut to the appropriate length and flattened (if formed on the cylindrical mandrel) for packaging, shipping and storage. Providing the wick 35 in a flat configuration rather than as a cylinder reduces the required shipping and storage space by as much as about 80%.

The cylindrical shape required for normal operation of the wick 35 is quickly restored by pressing the wick in opposite directions along the opposing creases and inserting it into the heater tube 31. The stiff nature of the inner layer of material allows the wick 35 to be easily "popped" open into a generally cylindrical shape.

When the wick 35 manufactured by the above techniques is restored to cylindrical shape, the outside diameter thereof will vary somewhat from wick to wick. This variation has not presented a problem because the wet swelling property of the wick provides for good thermal contact in spite of this outside diameter size variation. The absorbency of this laminate is such as to provide wicking of water in excess of 2 inches in height within 60 seconds when the bottom of the wick is placed in a shallow supply of water. The degree of swell when wetted is enough to provide a 1–3% increase in outside diameter.

Another form of wick 35 comprises a laminate of at least three layers of absorbent material, the innermost layer having good wet-strength properties and one of the outer layers having good wicking and swelling properties. In this embodiment, wick 35 comprises a composite outer layer of two sheets of 55 pounds basis weight Scott-Hi-Loft 3055 nonwoven paper and the two inner layers of Monadnock 1309-030 paper, a high wet strength paper having a basis weight of about 30 pounds. The three separate layers are laminated and lightly adhesively bonded together by wrapping each in turn at an angle around a forming cylinder to create a tightly formed "core" and cut to the desired lengths, similar to the process used in producing cores for toilet-tissue rolls. It will be appreciated that this method of manufacture produces a cylinder having an accurately dimensioned inside diameter but with variable outside diameters. Again, this does not present a problem because the wet swelling property of the wick provides for good thermal contact in spite of the outside diameter size variation. The absorbency of this laminate is such as to provide wicking in excess of 3 inches in height within 60 seconds when the bottom of the wick is placed in a shallow supply of water. The degree of swell of this wick when wetted is sufficient to provide 2–3% increase in outside diameter.

Another exemplary wick was made from paper manufactured with 100% Nersanier XJ pulp. Flat sheets of this paper, 5⅜ inches×4½ inches×0.040 inches thickness, were rolled into open-ended cylinders 4½ inches in length and approximately 1.75 inches in O.D. The cylinders were closed by heat-sealing a tape of polyester/polypropylene laminate film along the seam. The wet strength of this construction was marginal so that care had to be taken in removing a wet wick from the humidifier without tearing the wick. The paper swelled by about 85% in thickness when wetted resulting in an increase of outside diameter of about 0.035 inch, which provided good wet contact with the inner surface of heater tube 31. The wicks had a 2 inch wicking speed of about 2 minutes which was only fair but acceptable.

Other wicks were made by spirally winding four layers of N-2380 nonwoven webs, obtained from C. H. Dexter Division of Dexter Corporation, onto a mandrel to form a laminate. Portions of the web were lightly coated with adhesive to bond the laminate together. Each layer was about 0.10 inch thick. This wick swelled by about 33% in thickness when wetted resulting in an outside diameter increase of about 0.015 inch. The wetted wicks could be easily removed from the humidifier without tearing. The finished wick had a wicking rate of aout 3 inches in 2 minutes which was more than adequate.

The following is a brief description of the operation of the humidifier of the present invention. Before commencing use, the humidifier 10 is disassembled and the various components thereof sterilized or otherwise sanitized depending upon the hospital practice and/or the state of health of the patient upon which it is to be used. A new wick 35 is installed in heater tube 31 during reassembly of the humidifier, either before or after sterilization, the electronic controls connected and a water supply tubing from a source of sterile water connected to water inlet connector 21. Finally, appropriate respiratory tubing to the patient and to the respirator apparatus is connected to the air outflow connector 17 and the air inflow connector 16 of the humidifier 10, respectively. With the electrical supply cord connected to a suitable power source, the electronic controls are set and turned "on"—humidification begins almost immediately and 100% relative humidity of the exit gas is achieved within one or two minutes.

The temperature sensing thermistor 34 attached to the heating element 32 allows the electronic controller to cycle the electrical input to the heating element 32 "off" and "on" over short time intervals to control the temperature of said heater tube 31 within narrow limits which in turn controls the temperature of the saturated gases reaching the patient to within about 1° C. The control setting is adjusted by the operator according to the temperature of the saturated air reaching the patient. The relationship between setting and air temperature at the patient will depend upon the volumetric throughput of the system, a variable which changes from patient to patient.

The humidifier of the present invention normally provides respiratory gases to the patient at 100% relative humidity at a temperature of 25° to 40° C. at a continuous flow rate of from 1 to 60 liters per minute and a peak inspiratory flow rate of up to 100 liters per minute. Normally, because of the high evaporative rate, the surface of heater tube 31 will be at a fairly low temperature e.g., 160° F. compared to the higher temperatures found in other known humidifiers. However, if for any reason the temperature selected by the operator is too high or due to a failure in the thermostatic control circuit, the temperature of the air reaching the patient would rise, in which case the exit gas sensing element or the remote temperature sensor near the patient would shut the humidifier "off" and activate an audible and visual alarm. Shut-off of the humidifier normally occurs when the gas temperature reaching the patient exceeds 41° C. As a further safeguard, excessive temperature rise of the heat transfer surface of heater tube 31 causes the thermal cut-out device to shut off the humidifier power supply.

What is claimed is:

1. A sterilizable evaporative humidifier comprising a humidification chamber having an inlet port and an outlet port for gases, a liquid reservoir having a float valve for controlling the liquid level therein, a single-use, disposable porous evaporative element and a heating element isolated from said liquid reservoir, said humidification chamber having an internal volume of about 200 cc. and being surrounded by said heating element such that heat is transferred directly from the wall of said chamber to said porous evaporative element, said porous evaporative element being an open-ended cylinder having a vertical wicking rate of about two inches in the first minute and fitting loosely within said humidification chamber when dry and swelling into intimate contact with the side wall thereof when wet, one end of said evaporative element extending into said liquid reservoir to wick said liquid into the entire body of said evaporative element, said heating element being electronically controlled to provide respiratory gases to the patient at 100 percent relative humidity at a temperature of about 25° to 40° C. within two minutes of start-up, at a continuous flow rate of from about 1 to about 60 liters per minute and a peak inspiratory flow rate of about 10 to about 100 liters per minute, the pressure drop in said humidifier being about 0.1 cm. of water at a continuous flow rate of 30 liters per minute, with flow path of gases into and through said chamber being from said inlet port, along the interior surface of said porous evaporative element and thence through said outlet port, said humidifier being readily disassembled into its component parts for sterilization.

2. An evaporative humidifier according to claim 1 wherein said porous evaporative element comprises cellulosic material bonded together with a water insoluble adhesive.

3. An evaporative humidifier according to claim 2 wherein said porous evaporative element is a laminate of a highly liquid-absorbent cellulosic nonwoven paper and a dimensionally stable, absorbent high wet-strength paper.

4. An evaporative humidifier according to claim 3 wherein said porous evaporative element is flattened for shipping and storage, said evaporative element being restored to its original cylindrical shape by pressing along the creases and inserting same into the humidification chamber.

5. An evaporative humidifier according to claim 1 including electronic control means for interrupting the power supply to said humidifier when the temperature of the heating element or the gases at the patient exceeds a predetermined temperature level.

* * * * *